United States Patent [19]
Hijlkema

[11] Patent Number: 5,853,389
[45] Date of Patent: Dec. 29, 1998

[54] BALLOON CATHETER AND METHOD FOR MANUFACTURING

[75] Inventor: Lucas Johannes Hijlkema, Groningen, Netherlands

[73] Assignee: Cordis Corporation, Miami Lakes, Fla.

[21] Appl. No.: 6,860

[22] Filed: Jan. 14, 1998

Related U.S. Application Data

[62] Division of Ser. No. 612,340, Mar. 7, 1996, Pat. No. 5,792,415.

[51] Int. Cl.$^6$ .................................................. A61M 29/00
[52] U.S. Cl. ............................................. 604/96; 606/194
[58] Field of Search ............................. 604/96, 97–103, 604/280, 282; 606/191–194

[56] References Cited

U.S. PATENT DOCUMENTS

| | | |
|---|---|---|
| 3,097,058 | 7/1963 | Branscum et al. . |
| 4,878,495 | 11/1989 | Grayzel ............................... 604/101 X |
| 4,906,244 | 3/1990 | Pinchuk et al. . |
| 4,935,190 | 6/1990 | Tennerstedt . |
| 5,015,230 | 5/1991 | Martin et al. . |
| 5,041,125 | 8/1991 | Montano, Jr. . |
| 5,295,959 | 3/1994 | Gurbel et al. ........................ 604/103 X |
| 5,458,572 | 10/1995 | Campbell et al. ........................ 604/96 |
| 5,484,411 | 1/1996 | Inderbitzen et al. ...................... 604/96 |
| 5,545,132 | 8/1996 | Fagan et al. .............................. 604/96 |
| 5,718,684 | 2/1998 | Gupta ........................................ 604/96 |

FOREIGN PATENT DOCUMENTS

| | | |
|---|---|---|
| 0 304 258 | 8/1988 | European Pat. Off. . |
| 0 376 451 | 6/1989 | European Pat. Off. . |
| 0 439 202 A2 | 2/1990 | European Pat. Off. . |
| 2634382 | 7/1977 | Germany . |
| 42 17587 | 9/1967 | Japan . |

*Primary Examiner*—John D. Yasko
*Attorney, Agent, or Firm*—Gerstman, Ellis & McMillin, Ltd.

[57] ABSTRACT

The invention relates to a balloon for a catheter. The manufacturing of the balloon comprises providing of mold which has a mold cavity corresponding to an intended expanded form of the balloon member; placing opposite ends of a tube-like semimanufacture (parison) into securing elements for the purpose of securing their opposite end sections in the mold cavity; heating the semimanufacture; and generating a pressure difference between the inside and the outside of the semimanufacture to expand the balloon member against the walls of the mold cavity. In the molding, the end sections of the semimanufacture are twisted about an angle in relation to each other so that helical ridges are formed in balloon transition sections.

9 Claims, 3 Drawing Sheets

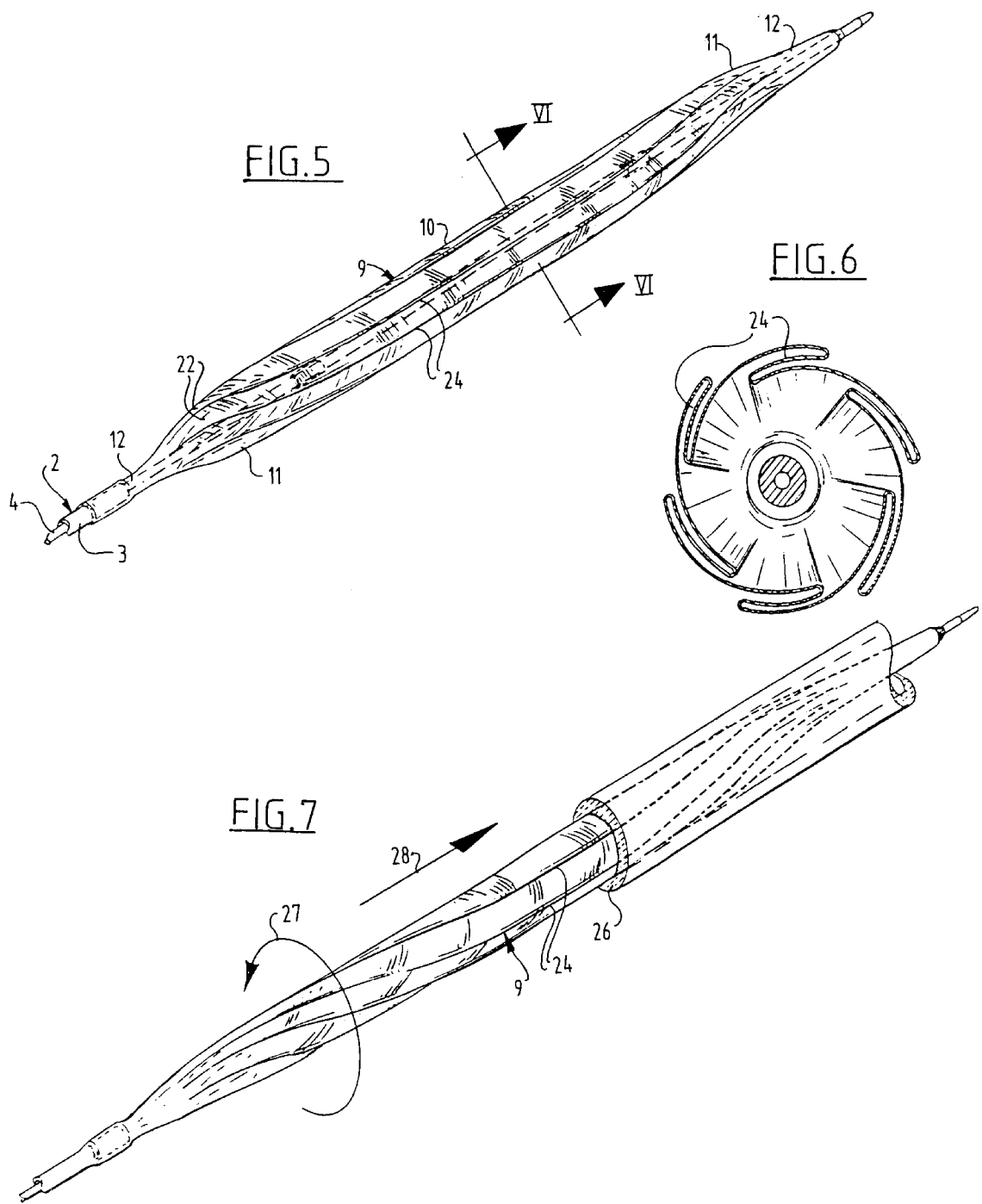

BALLOON CATHETER AND METHOD FOR MANUFACTURING

CROSS REFERENCE TO RELATED APPLICATION

This is a division of application Ser. No. 08/612,340, filed Mar. 7, 1996 now U.S. Pat. No. 5,792,415.

BACKGROUND OF THE INVENTION

The invention relates to a method for manufacturing a balloon catheter, in particular a balloon catheter with a very large balloon, as in known from U.S. Pat. Nos. 4,906,244 or 5,041,125.

The balloon for such a balloon catheter is made up of a central section with transition sections narrowing down to tube-like end sections on both ends thereof. The balloon is usually manufactured by means of blow-molding a tube-like parison or semi-manufacture. The wall of the semi-manufacture is relatively thick, so that sufficient material is available for the central section which is to be expanded.

In each transition section, the wall thickness decreases from that of the tube-like end section to that of the expanded central section. However, the wall of the transition section close to the end section is consequently still relatively thick, which considerably impedes the folding of the balloon into a small diameter. This folding into a small diameter is desirable, however, in order to be able to introduce the balloon catheter properly into a patient.

What is more, the wall thickness in the transition section does, in general, not decrease uniformly. There will be sections with a relatively thick wall separated from each other by sections with a relatively thin wall. This further impedes the folding of the balloon into a small diameter.

An object of the invention is to provide a balloon catheter and a method for manufacturing such a balloon catheter, resulting in a balloon which can be properly folded into a small diameter.

DESCRIPTION OF THE INVENTION

This aim is achieved by blow-molding the balloon while the parison is in axially twisted condition in the mold. By this, ridges of material extending spirally from the end section are formed on blow molding expansion in the transition section of the balloon member, where the walls are thicker than the wall of the central section. As a result, the transition section can be folded together very easily into a small diameter.

The tube-like parison or semi-manufacture is preferably manufactured by extrusion, and may be prestretched before it is received in the mold, to obtain the optimum properties required for the ensuing blow-molding process.

An advantageous further development is characterized by heating and expanding said balloon member, and transferring said heated, expanded balloon member to a second blow mold where its final shape is provided. Thus, the blow-molding process is carried out into two stages. An optimum distribution of material can thus be achieved in the end product.

During the blow molding, including both of the blow molding steps where a two step process is used, the end sections of the parison and balloon are axially twisted relative to each other to a degrees of about 90° to 1440° (four complete twists), for example about 270 degrees, by placing the tubular parison that forms the balloon member into axially twisted configuration. During blow molding, a number of evenly distributed spiral ridges of material is spontaneously obtained. There are approximately 5 to 15 of them created by this process for example, ten ridges.

Specifically the tubular parison may be twisted to an angle which is dependent upon the length of the balloon member produced. The original tubing from which the parison is formed may be 37 cm. in length, for example. The tubing is formed, stretched, and then cut to provide a balloon portion which is inserted into the blow mold. If the balloon is 8 cm. long, the total angle of twist of the 37 cm. tubing may be about 90°. If the balloon is 2 cm. long, the tubing may be twisted four complete times, so that a similar angle of twist is provided in both the 8 cm. balloon and the 2 cm. balloon. However, other angles of twist may be used as well.

A further advantageous development is characterized by turning the end sections in the direction that causes the semi-manufacture or parison to be twisted in the direction of a clockwise helix.

As a result of twisting, the ridges of material extend out in a spiral pattern. Thus, the introduction of the catheter into the patient, and the removal thereof later on, can be facilitated by rotating the catheter about its longitudinal axis. The spiral ridges of material in the folded balloon state extend in a helical pattern and support, on rotation, the movement in a longitudinal direction by a screw action.

The invention also relates to and provides a balloon catheter manufactured in accordance with the method as characterized. The balloon member comprises a central section with transition sections extending to tube-like end sections. By this invention, at least one of the transition sections comprise spirally extending ridges of material extending from the end sections toward the central section.

An advantageous small diameter of the balloon member of this invention can be achieved by the central section and the transition sections, folded in pleats against each other in a small diameter, folded configuration. The pleats are formed by and comprise the spirally arranged ridges of material. A very gradual transition without bulges is achieved from the end sections to the folded central section.

Additional advantageous properties and advantages of the invention will become apparent upon reading the following description of an example of an embodiment with reference to the attached drawings.

DESCRIPTION OF THE DRAWINGS

FIG. 5 is a perspective view of the balloon member of FIG. 3 in the folded state;

FIG. 6 shows a cross-section along the line VI—VI of FIG. 5; and

FIG. 7 is a perspective view of the folded balloon catheter of FIG. 6 being advanced through an introducer catheter.

DESCRIPTION OF SPECIFIC EMBODIMENTS

Figure 1:
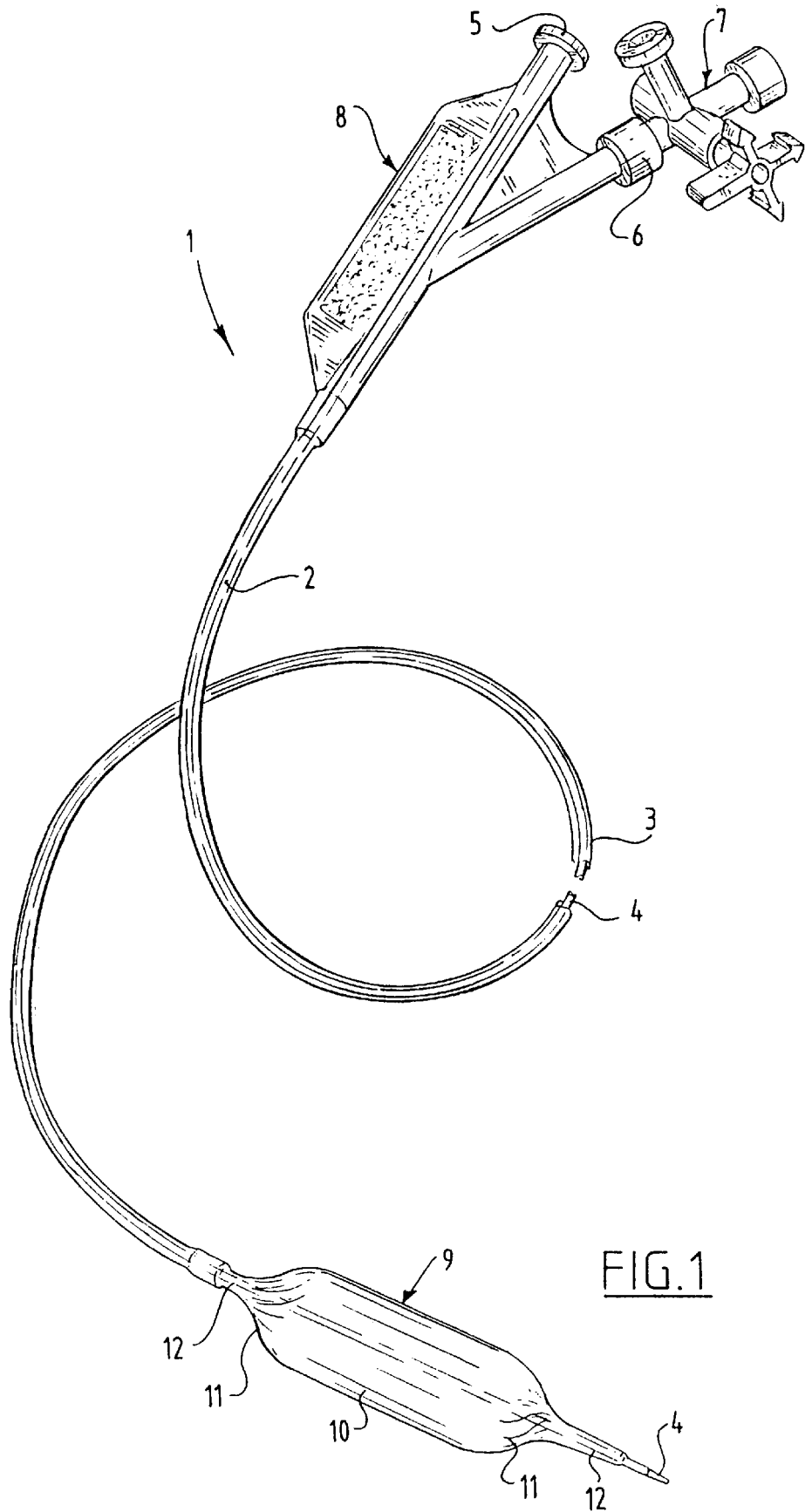
FIG. 1 shows a catheter manufactured with the method according to the invention in a partly broken away perspective view.

The catheter 1 shown in FIG. 1 comprises a tube-like basic tubular body 2 which has been assembled from an outer tube-like element 3, in a central lumen in which an inner tube-like element 4 has been received. The tube-like element 4 also comprises a lumen.

At the proximal end of the catheter 1 a connecting element 8 has been arranged. This connecting element 8 has two connections 5 and 6. The connection 5 is connected with the lumen of the inner tube-like element 4, and the connection 6 is connected with the lumen of the outer tube-like element 3, that is to say, a channel with annular cross-section formed by the space outside of inner tube-like element 4 and inside the lumen of the outer tube-like element 3.

As can be seen in the figure, a known closure 7 can be provided to the connection 6.

At the distal end of the catheter 1 is a balloon member 9. This may be a balloon with a relatively large inflated diameter such as 15–30 mm.

The balloon member 9 has a tubular central section 10 with transition sections 11 on either side turning into end sections 12.

The balloon member 9 has been manufactured in a blow-molding process by the method according to the invention. This step will be explained in greater detail with reference to FIG. 2.

Figure 2:
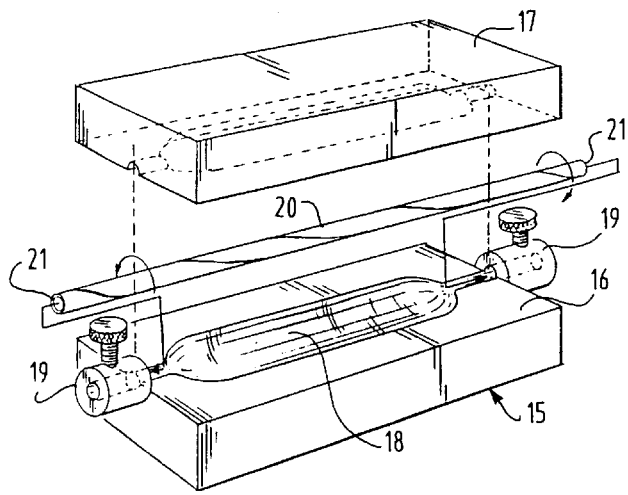
FIG. 2 illustrates schematically one step of the method according to the invention.

In FIG. 2, a mold 15 has been illustrated schematically, comprising two mold sections 16, 17. In the mold sections 16 and 17, a mold cavity 18 has been provided, the shape of which corresponds with that of the intended expanded form of the balloon member to be manufactured. At opposite ends this mold cavity 18 forms securing elements 19. In the securing elements 19 the end sections 21 of a tube-like parison or semi-manufacture 20 are secured.

As is indicated by the arrows, the semi-manufacture 20 is twisted before it is received in the mold 15. For this purpose the end sections 21 are twisted over a certain angle in relation to each other. A typically suitable angle is one of 270°.

After receiving the semi-manufacture 20 in the mold 15, a pressure difference between the inside and the outside of the semi-manufacture 20 is generated by blowing in a conventional manner not explained in greater detail here, for instance by connecting the bore defined inside the semi-manufacture 20 to a source of gas under pressure. At the same time the semi-manufacture is heated to a temperature higher than its softening temperature, so that it will be "blown up". The inflated section of the semi-manufacture 20 arranges itself against the wall of the mold cavity 18 and thus obtains its intended, expanded form.

Next, one can allow the semi-manufacture to cool down, while the expanded form is retained under pressure. Because of the flexibility of the material of which the semi-manufacture has been made, which is a plastic material such as nylon, the balloon member formed can then be collapsed, folded, and expanded again afterwards by increasing the pressure inside.

Figure 3:
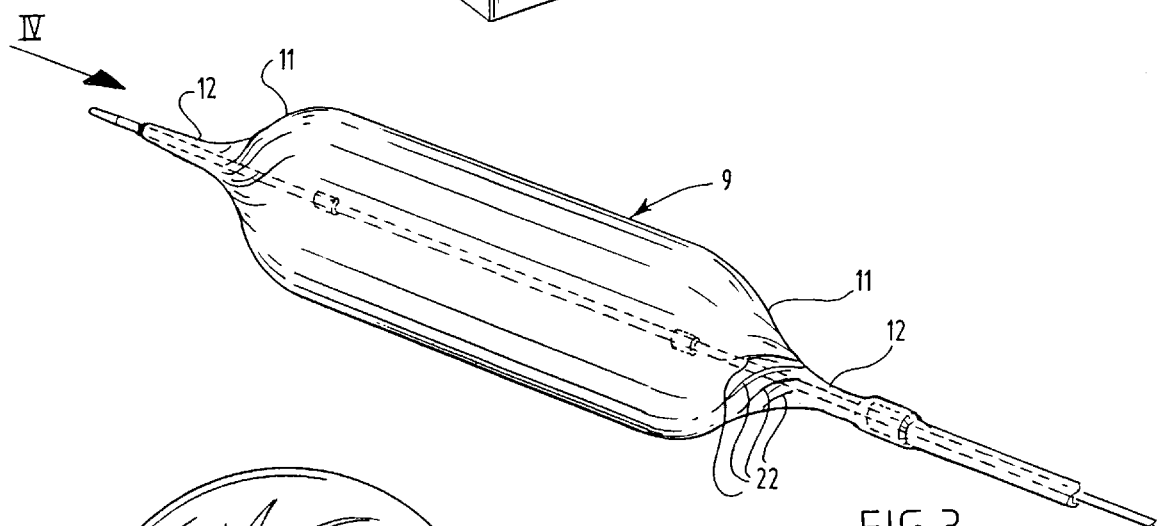
FIG. 3 is a large-scale perspective view of the balloon member of the catheter of FIG. 1.
Figure 4:
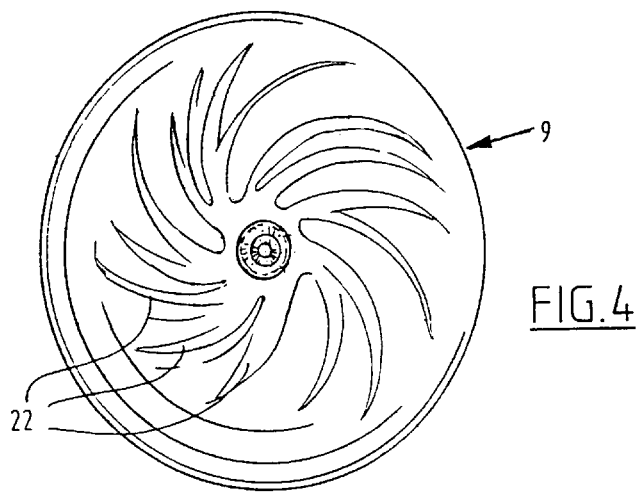
FIG. 4 shows a front elevational view of the balloon member of FIG. 3 in the direction as indicated by arrow IV of FIG. 3.

FIG. 3 is a large-scale drawing of the balloon member thus formed. Because the semi-manufacture 20 has been received in the mold 15 in the twisted manner described above, ridges of material 22 have been formed in the transition sections 11 extending spirally inwardly from the end sections 12. The ridges of material 22 are relatively thick, whereas the material in between is stretched out and thinner. The ridges of material 22 have been shown once more in FIG. 4 for the sake of clarity.

The ridges of material 22 can, to a certain extent, be compared with the spokes of an umbrella. They can fold against each other, whereby the thinner material in between is folded into pleats. Thus, in folded state, a small diameter can be achieved.

This folded state is illustrated in the FIGS. 5 up to and including 7.

As can be seen in the FIGS. 5 and 6, the central section 10 and the transition sections 11 are folded in pleats against the inner tube-like element 4 of the basic body 2. The folds 24 fit closely together and substantially coincide with the fan-shaped ridges of material 22.

As can be seen in FIG. 5 as well that the outer tube-like element 3 of the basic body 2 is shorter than the inner tube-like element 4. The relatively proximal end section 12 of the balloon member 9 is connected with the end of the outer tube-like element 3, whereas the relatively distal end section 12a of the balloon member 9 is connected with the inner tube-like element 4. The inside of the balloon member 9 is therefore connected via the remaining channel with the annular cross-section inside the outer tube-like element 3 and outside of tube 4 with the connection 5 of the connecting member 8. By supplying via this connection a gas or liquid under pressure, the balloon 9 can be unfolded into its expanded form. This occurs following introduction of the catheter into a patient for the purpose of dilation or occlusion of a blood vessel.

Introduction occurs in the usual manner via a conventional introducer sheath 26, which has been illustrated schematically in FIG. 7. This introducer sheath 26 can have a relatively small inside diameter, as the balloon member 9 can be folded into a small diameter and because no bulges are formed at the transition sections as a result of unevenly distributed material.

As a result of the ridges of material extending in a spiral shaped manner and the closely fitting folds, sections with a helically shaped profile are formed on either side of the balloon member. By rotating the catheter in a suitable manner, as indicated by arrow 27, a certain force 28 can be generated with screw action by ridges 22, which facilitates the introduction of the catheter. Also the removal of the catheter can take place smoothly by applying a correct rotation.

Although the method according to the invention is explained with reference to FIG. 2, in which a balloon member is formed in one single blow-molding step, it is also possible to achieve the same in more steps. A first initiation can, for example, be carried out in the form of a limited expansion in order to obtain a second semi-manufacture with a suitable material distribution. This second semi-manufacture can then be expanded in a second blow-molding step to obtain the intended ultimate form. In that case the suitable material distribution is achieved during the first step by the right choice of mold cavity of the mold in which this step is performed.

The ridges 22 thus formed in the mold may not be produced by any corresponding ridges in the mold, but may be produced purely by the twisting of the parison.

The above has been offered for illustrative purposes only, and is not intended to limit the scope of the claims below.

That which is claimed:

1. A balloon which comprises a tubular central section and, when inflated, frustoconical transition sections on either end of the central section connecting with tubular end sections of less diameter than the central section, said transition sections comprising spiral ridges of material extending from each end section toward the central section, and in which, in deflated condition, the central section and the transition sections are folded in pleats as urged by said spiral ridges.

2. The balloon of claim 1 in which, in said delated condition, said pleats comprise folded wall sections extending along most of the length of said balloon, said folded wall sections comprising three separate, connected wall portions lying together in three generally parallel, circumferentially extending layers in a wall section, to substantially reduce the diameter of said deflated balloon when compared with said balloon in fully inflated condition.

3. The balloon of claim 2 in which said spiral ridges are of differing shapes and of uneven distribution.

4. The balloon of claim 1 in which said spiral ridges are of differing shapes and uneven distribution.

5. The balloon of claim 4 in which each transition section comprises between five and fifteen spiral ridges.

6. A tubular catheter balloon comprising a flexible, tubular wall, in which, in deflated condition, said balloon wall comprises folded wall sections extending along most of the length of said balloon, said folded wall sections comprising three separate, connected wall portions lying together in three generally parallel, circumferentially extending layers in a wall section, to substantially reduce the diameter of said deflated balloon when compared with said balloon in fully inflated condition.

7. The catheter balloon of claim 6 in which said balloon defines tubular ends of reduced diameter when compared with the remainder of said balloon in fully inflated condition, and a generally frustoconical transition section adjacent each balloon end connecting each reduced-diameter end with a central balloon portion, said transition section defining generally spirally arranged ridges of differing shapes and uneven distribution.

8. A tubular catheter balloon, said balloon comprising a flexible, tubular wall capable of assuming an inflated condition and a deflated condition, said balloon in inflated condition defining a generally frustoconical transition section adjacent each balloon end connecting a reduced-diameter balloon end with a central balloon portion, said transition section defining generally spirally arranged ridges of differing shapes and uneven distribution.

9. The balloon of claim 1 wherein the ridges of material are substantially evenly distributed around the circumference of the transition section.

\* \* \* \* \*